(12) United States Patent
Mosig et al.

(10) Patent No.: US 10,731,119 B2
(45) Date of Patent: Aug. 4, 2020

(54) METHOD AND DEVICES FOR THE IN VITRO PRODUCTION OF ARRANGEMENTS OF CELL LAYERS

(71) Applicant: Universitaetsklinikum Jena, Jena (DE)

(72) Inventors: Alexander Mosig, Jena (DE); Knut Rennert, Jena (DE)

(73) Assignees: Universitaetsklinikum Jena, Jena (DE); Microfluidic ChipShop GmbH, Jena (DE)

( * ) Notice: Subject to any disclaimer, the term of this patent is extended or adjusted under 35 U.S.C. 154(b) by 219 days.

(21) Appl. No.: 15/309,586

(22) PCT Filed: May 7, 2015

(86) PCT No.: PCT/DE2015/100183
§ 371 (c)(1),
(2) Date: Nov. 8, 2016

(87) PCT Pub. No.: WO2015/169287
PCT Pub. Date: Nov. 12, 2015

(65) Prior Publication Data
US 2017/0226457 A1 Aug. 10, 2017

(30) Foreign Application Priority Data
May 8, 2014 (DE) .......................... 10 2014 106 423

(51) Int. Cl.
*C12M 1/12* (2006.01)
*C12M 1/00* (2006.01)
(Continued)

(52) U.S. Cl.
CPC ............ *C12M 25/02* (2013.01); *C12M 21/08* (2013.01); *C12M 23/12* (2013.01); *C12M 23/16* (2013.01);
(Continued)

(58) Field of Classification Search
None
See application file for complete search history.

(56) References Cited

U.S. PATENT DOCUMENTS 4,559,299 A    12/1985   Rotman
5,190,878 A *   3/1993   Wilhelm ................ C12M 23/44
                                                                                                    435/297.2
(Continued)

FOREIGN PATENT DOCUMENTS

CA          2387549 A1    2/2001
DE          3923279 A1    1/1990
(Continued)

OTHER PUBLICATIONS

Japanese Office Action for corresponding Patent Appln. 2017-510723 with English Translation.

*Primary Examiner* — Erin M. Bowers
(74) *Attorney, Agent, or Firm* — Duane Morris LLP

(57) ABSTRACT

The invention is directed to a method for the in vitro production of arrangements of cell layers in which a first well (2.1) which is closed off from its environment except for a first inlet opening (4.1) and a first outlet opening (5.1) and which has as a first cell substrate (6.1) a first wall (2.1.1) and as a second cell substrate (6.2) an opposite, second wall (2.1.2) which is separated from the first wall (2.1.1) by a first gap, a free surface of a cell substrate (6.1, 6.2) to be colonized with cells is oriented orthogonal to the Earth's gravitational force, and cells (9) are adhered to the cell substrate (6.1, 6.2) to be colonized. The invention is further directed to a method of maintaining the biological functionalities of the cell layers and semi-finished products of a device for the in vitro production and culturing of cell layers and a method for the production of the device.

1 Claim, 7 Drawing Sheets

(51) Int. Cl.
*C12M 1/42* (2006.01)
*C12M 1/34* (2006.01)
*C12M 3/06* (2006.01)
*C12N 5/00* (2006.01)
*C12M 3/00* (2006.01)
*C12M 1/32* (2006.01)
*C12N 5/071* (2010.01)

(52) U.S. Cl.
CPC ............ *C12M 23/34* (2013.01); *C12M 29/10* (2013.01); *C12M 35/04* (2013.01); *C12M 35/08* (2013.01); *C12M 41/36* (2013.01); *C12M 41/46* (2013.01); *C12N 5/0062* (2013.01); *C12N 5/0068* (2013.01); *C12N 5/0697* (2013.01); *C12N 2525/00* (2013.01)

(56) References Cited

U.S. PATENT DOCUMENTS

| | | |
|---|---|---|
| 7,560,274 B1 | 7/2009 | Fuller et al. |
| 8,357,528 B2 | 1/2013 | Vacanti et al. |
| 2007/0037277 A1 | 2/2007 | Shuler et al. |
| 2007/0212773 A1 | 9/2007 | Fujii et al. |
| 2009/0023608 A1 | 1/2009 | Hung et al. |
| 2010/0216244 A1 | 8/2010 | Wu et al. |
| 2011/0091930 A1 | 4/2011 | Vacanti et al. |
| 2011/0136218 A1 | 6/2011 | Ahluwalia et al. |
| 2014/0038279 A1 | 2/2014 | Ingber et al. |

FOREIGN PATENT DOCUMENTS

| | | |
|---|---|---|
| DE | 19935643 A1 | 2/2001 |
| DE | 10032808 A1 | 1/2002 |
| DE | 102009035502 A1 | 2/2011 |
| JP | 2007/020486 * | 2/2007 |
| JP | 2007020486 A | 2/2007 |
| WO | WO 84/03047 A | 8/1984 |
| WO | 2007012071 A1 | 1/2007 |
| WO | 2012032646 A1 | 3/2012 |
| WO | WO 2012/032646 * | 3/2012 |
| WO | 2013085909 A1 | 6/2013 |

* cited by examiner

Section plane A - A

Section plane B - B

METHOD AND DEVICES FOR THE IN VITRO PRODUCTION OF ARRANGEMENTS OF CELL LAYERS

RELATED APPLICATIONS

The present application is a U.S. National Stage application of International PCT Application No. PCT/DE2015/100183 filed on May 7, 2015 which claims priority benefit of German Application No. DE 10 2014 106 423.2 filed on May 8, 2014, the contents of each are incorporated by reference in their entirety.

BACKGROUND OF THE INVENTION

The invention is directed to a method and devices for the in vitro production of arrangements of cell layers.

Various methods and devices are known for the in vitro production of arrangements of cell layers and culturing thereof. Cell culture inserts only allow cellular processes to be studied under static conditions. Accordingly, there is an enrichment of catabolic substances over the respective cell cultures so that their growth and vitality are reduced and limited in time. Since culturing is possible only under static conditions, no shear forces can be generated through liquids at the cells. However, these shear forces are necessary for a large number of cells so that they adopt physiologically correct properties such as occur, for example, in the human body.

Cells and tissues can be perfused in the Boyden chamber so that enrichment of catabolic substances is prevented, fresh nutritive media can be supplied to the cells or tissues, and the above-mentioned shear forces can be generated at the cells or tissues. However, this system has the grave disadvantage that the cells are efficiently perfused by nutrient medium from one side only (mostly apical). The cells cannot be perfused basolaterally. This also reduces and temporally limits cell growth and cell vitality. Further, the system is limited to culturing at most a two-dimensional cell area or tissue area.

Due to its design features, the arrangement described in US 2011/0091930 A1 allows the culturing of a maximum of only one cell layer. Further, as a result of the construction, no direct microscopy of the cells can be carried out under perfusion conditions in the well because supplying channel systems below the surface of the culture impede the optical observation axis of the microscope.

While the arrangement described in DE 10 2009 035 502 A1 allows cells and tissues to be observed under flow conditions, the wells cannot be perfused individually through separate liquid flows. Further, because of its design features, the system is not suitable for providing a plurality of culturing surfaces for cells in a well so that the interaction between different cell layers, which is important for a realistic picture of the functioning of organs in vitro, cannot be sufficiently taken into account.

The technical teaching from U.S. Pat. No. 8,357,528 B2 allows culturing of oppositely located cell layers on a porous formation such as a membrane, for example. The membrane separates two culture chambers from one another vertically. Based on the construction of the chamber system, it is not possible, for example, to observe the adhesion and/or transmigration of cells directly through a microscope. The system is limited to receiving two cell layers. Usually, at least three cell layers are required to model a multilayered organoid structure.

Possibilities described in US 2007/0037277 A1, US 2009/0023608 A1 and US 2010/0216244 A1 are also limited to two cell layers.

SUMMARY OF THE DISCLOSURE

It is the object of the invention to suggest a further possibility for the in vitro production and arrangement of cell layers by which cell layers can be arranged, cultured and studied in a predetermined manner. It is likewise the object of the invention to suggest a device by which complex arrangements of cell layers can also be cultured and studied.

This object is met through the subject matter of the independent claims. Advantageous embodiments are indicated in the dependent claims.

The object is met in a method for the in vitro production of arrangements of cell layers having the following steps:

A providing a first well which is closed off from its environment except for an inlet opening and an outlet opening and which has as a first cell substrate a first wall and as a second cell substrate an opposite, second wall which is separated from the first wall by a gap, B aligning the first well in such a way that a free surface of a cell substrate to be colonized with cells is oriented orthogonal to Earth's gravitational force, C filling the first well with a cell suspension containing the cells, sedimenting the cells on the cell substrate to be colonized, and adhesion of the cells to the cell substrate to be colonized so that a first cell layer is formed, D realigning the first well so that a cell substrate to be colonized with cells is oriented orthogonal to Earth's gravitational force, wherein the cell substrate to be colonized is either the cell substrate that has already been colonized or the other cell substrate, E refilling the first well with a cell suspension containing the cells, sedimenting the cells on the cell substrate to be colonized and adhesion of the cells to the cell substrate to be colonized so that a further cell layer is formed, and F repeating steps D and E until a desired arrangement of cell layers is produced in the first well.

By "well" is meant hereinafter a depression. It can be enclosed by adjoining walls and can form a space. Tops of the walls form edges of the well.

A cell substrate is a surface comprising a man-made or natural material to which cells adhere and can survive if appropriately supplied physiologically. Cell substrates are, for example, surfaces of plastic, metal or glass (man-made materials). Cell substrates can also be cell layers, tissue layers or surfaces covered with biomolecules, for example, biopolymers, (natural materials). Cell substrates made of man-made materials can have a surface texturing, for example, a roughness or a coating (e.g., anionic/cationic, hydrophobic/hydrophilic, proteins, polymers, cells) which promotes adhesion.

If the opposite surfaces of the walls are separated from one another and a gaseous or liquid medium, hereinafter also referred to as fluid, can flow therebetween, there is a gap between the two walls. This gap can be reduced while the method according to the invention is being carried out through growing cell layers.

In the method according to the invention, the cells are arranged on a cell substrate to be colonized by utilizing the action of gravitation. The cells sediment on the cell substrate to be colonized, where they adhere. The adhering cells are accordingly bonded to the cell substrate and will remain on the cell substrate when the cell suspension flows out and when the orientation of the well changes.

A cell layer is present when at least some cells adhere to the cell substrate. Therefore, the cell substrate can be completely covered by cells from a cell suspension. Depending on the prevailing physiological conditions, the quality of the cell substrate and the biological, biochemical and biophysical characteristics of the cells of the cell suspension, only a part of the surface of the cell substrate, for example, 5%, 25%, 50% or 75%, may be covered. A cell culture is formed by one or more cell layers.

Cells of one cell type may be present in a cell suspension. In other configurations of the method according to the invention, it is also possible for cells of different cell types to be present in a cell suspension.

The method according to the invention makes it possible to colonize cell substrates with cells. In so doing, series of cell layers can be arranged successively on one or more of the cell substrates. The wells can accordingly be ordered in a predetermined manner with cell layers of selected cell types in predetermined sequences of layers and in a predetermined configuration of cell layers or series of cell layers of different cell substrates. These possibilities are limited merely by the available space and the compatibility of the cell layers with one another, particularly when a cell layer is used as a cell substrate to be colonized.

It is advantageous that the cell layers can be arranged on the cell substrate inside the well. Therefore, it is not necessary to colonize the individual cell substrates separately and only then produce the well through assembly, in that, for example, the cell substrates are positioned opposite one another. Further, as a result of the method according to the invention, the risk of damaging or otherwise physically affecting the cell layers during assembly is prevented.

As has already been mentioned, it is possible to use cell suspensions with cells of different cell types in steps C and E so that at least the first cell layer and a further cell layer are formed by cells of different cell types.

The method according to the invention can advantageously be used to produce organoids. Organoids are artificial replications of organs or of individual regions of an organ, for example, of a liver sinusoid.

Used for this purpose is a device having a first well and a second well. Like the first well, the second well has as cell substrate two opposing walls which are separated from one another by a gap, and the second wall of the first well is formed by a first lateral surface of a porous membrane, and a second lateral surface of the membrane serves as a wall of the second well. At least one cell layer of one cell type is produced on at least two of the cell substrates.

It is possible to maintain the biological functionalities of the cell layers of an arrangement of cell layers or of an organoid produced according to one of the above-described methods according to the invention in that a first fluid flow is guided through the first chamber and a second fluid flow is guided through the second chamber, wherein the first fluid flow and the second fluid flow contain nutrients.

Nutrients are, for example, caloric equivalents, sugar, ATP, NADP, NADPH or growth factors, hormones, enzymes, synthetic active ingredients and the like.

In this respect, it is particularly advantageous when a device is used in which the second wall and the cell substrate of this second wall are formed by a porous membrane. In this case, the cell layers on the second wall can be supplied through perfusion through the first well and through the second well.

The flow ratios in the first well and second well can be influenced by the selection of the shape of the wells. Accordingly, a laminar flow of the first fluid flow through the first well and of the second fluid flow through the second well is achieved through an elongated shape of the first well and second well.

A turbulent flow of the first fluid flow through the first well and of the second fluid flow through the second well is achieved through a round shape of the first well and second well.

The flow ratios can be additionally influenced through the dimensioning, arrangement and orientation of inlets and outlets at the wells.

Advantageously, it is made possible that the material compositions of the first fluid flow and/or second fluid flow are adjusted in a controlled manner and measurement data are taken at the cell layers.

The measurement data of chemical and/or physical parameters can be acquired at least at a first fluid flow and second fluid flow. This is preferably carried out as they exit from the first well or second well. The measurement data can be used to control the material compositions of the first fluid flow and/or second fluid flow but also to draw conclusions about the processes in the cell layers in the wells. These possibilities for detecting and evaluating measurement data make a testing method possible.

In a further embodiment of the method, the measurement data can be acquired by impedance measurements.

It is further possible that the membrane is bent by adjusting different pressure ratios in the first well and second well, and the amount of bending and the direction of bending are controlled by adjusting the pressure ratios. As a result of this possibility, cells of the cell layers which are present on the membrane can be elongated or compressed. This makes it possible to allow a mechanical stress to act on the cells in a specific manner.

The above-stated object is further met through semi-finished products of a device for in vitro production and culturing of cell layers. These semi-finished products have two first wells and second wells which are arranged one above the other and are separated from one another by a porous membrane with two lateral surfaces, wherein one wall is formed as a cell substrate of the first well through a lateral surface of the membrane and one wall is formed as a cell substrate of the second well through the other lateral surface. The first well has at least one inlet opening for ingress of a first fluid flow of a first fluid into the first well and at least one outlet opening for egress of the first fluid flow out of the first well, and the second well has at least one inlet opening for ingress of a second fluid flow of a second fluid into the second well and at least one outlet opening for egress of the second fluid flow out of the second well.

The fluids can be cell suspensions and/or nutritive media, for example. Their properties, for example, their chemical and/or physical composition, temperature, viscosity can be changed in a temporally regulated or controlled manner.

Semi-finished products are concrete products which constitute a separate technical unit only after further processing and/or assembly with other semi-finished products or devices.

It is possible to provide the wells of a semi-finished product with a liquid-tight seal, preferably a liquid-tight and gas-tight seal, by which the wells are sealed against the environment. As a result of liquid-tight sealing with a foil (bonding), at least one chamber is formed from the semi-finished product, which chamber is divided by the membrane into at least a top chamber half and a bottom chamber half corresponding to the first well and second well.

A device for in vitro production and culturing of cell layers is characterized in that either two or at least three semi-finished products are mounted one above the other and connected to one another in a liquid-tight manner along mutually abutting edges of the first wells and second wells, and the wells facing outward into an environment of the device are covered by a wall and are sealed in a liquid-tight manner from the environment.

In a further-reaching and advantageous embodiment of the device, it can have measurement points for fluorescence-based, contactless acquisition of measurement data. For example, the method which has already been described above can be implemented by means of these measurement points.

In a very advantageous further development of the device, each of the inlet openings can be fluidically connected to an outlet opening of another chamber so that first fluid flows and second fluid flows flow through a plurality of first wells and/or second wells. A configuration of this kind makes it possible for the user to connect a plurality of wells.

The semi-finished products according to the invention can be assembled to form a device for in vitro production and culturing of cell layers in that two of the semi-finished products are mounted one above the other and are connected to one another in a liquid-tight manner along abutting edges of the first wells and second wells, and the wells facing outward into an environment of the device are covered by a wall and sealed in a liquid-tight manner from the environment.

A liquid-tight seal against the environment is possible, for example, by means of a foil which is put over the corresponding well and connected, e.g., glued or bonded, to edges of the well.

It is also possible that at least three of the semi-finished products are mounted one above the other and connected to one another in a liquid-tight manner along mutually abutting edges of the first wells and second wells, and the wells facing outward into an environment of the device are covered by a wall and sealed in a liquid-tight manner from the environment.

The devices according to the invention can also be constructed as a chip, also known as biochip. In this regard, at least one well is provided on a support which, for example, has the dimensions of a specimen slide such as is known from light microscopy.

The chip comprises at least one well which can be connected through a microchannel system to other wells on the same chip or on further chips. In each well, a fluid flow can be generated in that a fluid, e.g., a cell suspension or a solution with nutrients, flows from the inlet opening through the well to the outlet opening. Because of the existing membrane, cell layers on the membrane of every well can be supplied with nutrient medium additionally through a lower microchannel system independent from other wells on the biochip. Located in every well is a membrane which is porous and self-supporting and whose material constitution and utilized pore size and pore density are selected in such a way that it is possible to completely colonize the membrane with cells. It is very advantageous when the quality of the membrane at the same time allows observation of the cells using light microscopy without increased light absorption or light scattering. This results, for example, in that the membrane is transparent, which is achieved for example, but not exclusively through materials such as polyester (PET) or polycarbonate (PC) or polydimethylsiloxane (PDMS).

The chip is preferably made of biocompatible material, for example, cyclic olefin copolymers (e.g., ZEONOR® or TOPAS®). The utilized materials allow the cells or tissue located in the chip to be analyzed by fluorescence microscopy without interfering autofluorescence.

The semi-finished products according to the invention advantageously provide the possibility of supplying cell layers located on the membrane or membranes with nutrients through the membrane in devices according to the invention. This supply, which can also be referred to as base perfusion or basal perfusion, also allows thicker and more complex arrangements of cell layers to be built while simultaneously ensuring supply to the lowest cell layers near the membrane also.

It is possible that a medium is guided from the outlet opening of a well entirely or partially to the inlet opening of the well again. For example, a basal perfusion can be achieved with a limited amount of medium through a fluidic short circuit of this kind.

The present invention describes a microfluidic chip system which is preferably constructed in the standardized specimen slide design. Accordingly, use with standardized hardware for liquid handling and analysis common in laboratories is possible. The system combines the respective advantages of the existing systems such as cell culture inserts (Transwell© system) and the Boyden chamber.

Owing to construction, two individual chips can be combined with one another to form a chamber body with two membranes. The system allows up to four separate cell layers or tissue layers to be cultured and perfusion of the system via up to three independent channel systems. Based on the construction of the device, only small volumes are needed for studies. Further, non-contacting, non-destructive studies of cellular processes within the biochip, e.g., detailed microscopic and/or spectroscopic analyses, are possible. The chip serves as basis for the configuration of replicas of the structure and function of blood vessels, liver, intestine, and a tumor model. These specific construction features and abstracted models of organ structures and the functional modeling thereof in the microfluidic chip are likewise the subject matter of the invention.

With devices according to the invention and by applying the method according to the invention, it is possible, for example, to dynamically join different tissues or even organoids. For example, a tissue or an organoid can be provided in a well or in a device according to the invention having two or more wells. These wells are connected to further wells in that their outlet openings are connected through lines to inlet openings of other wells. Identical or different tissue or organoids may be present in the other wells. A medium which has flowed through a well with a tissue or organoid subsequently arrives in another well in which an identical or different tissue or organoid is present. For example, it is possible that a liver-intestine axis is built in that cell layers of the liver are provided in a first device according to the invention and cell layers of the intestine are provided in a second device according to the invention. A medium or, depending on the construction, and experimental configuration of the liver-intestine axis, a plurality of media arrive in the second device after flowing through the first device. Physiological processes can be recreated artificially and compactly through an arrangement of this kind.

The devices according to the invention and the method according to the invention make it possible to mimic complex organoid structures, for example, but not exclusively, of the liver sinusoid, blood vessels, intestine, or structures of tumors and the blood vessels supplying them. In this respect, determining parameters of the cell culture such as nutrient medium composition, flow rate of the perfused medium, oxygen saturation and/or carbon dioxide saturation, pH and temperature can be easily monitored because of the small volumes. Since the fluid flows supplying the cell layers and tissue layers are controllable independent of one another, the above-mentioned cell culture parameters can be adjusted individually for each well and different tissue layers can be perfused within a well under different conditions. This makes it possible to adapt to the individual experiment requirements in an optimal manner. Accordingly, for example, cell layers or tissue layers having different requirements for cell culture medium can be cultured simultaneously in a well and their interaction can be studied.

In an advantageous construction, the system can be outfitted with a sensor arrangement, for example, for pH values and partial gas pressure measurements in the medium. Further, electrodes can be provided, for example, vapor-deposited, on the bonding foils to make inferences about the cell colonization density, cell function and/or cell vitality on the individual membranes via electric resistance measurements. Further, the chips can be connected to one another in series or in parallel modularly via tube systems in order, for example, to study the interaction between various organoids.

The structure of the chip makes it possible to construct multilayer cell arrangements for the technical modeling of an organ structure and to mimic this organ structure for purposes of diagnostics, substance testing or investigation of molecular signal processes between or within cells and tissues. Structures of different organs can be simulated within the chip and can be connected via microfluidic circuits so that communications processes of the body can be recreated in the technical solution of the microfluidic chip.

An advantage of the invention is the possibility of modeling human organs, for example, but not exclusively, the liver, intestine or blood vessels in a microfluidics-based chip. This biochip system comprises the microfluidics-based chip and a quantity of cells and/or tissues which together form at least two and preferably three layers which are independent from one another and cultured in a common well. The biochip is designed for biomedical research for the study of cellular aspects of human organoids. Fields of application include, for example, but not exclusively, screening for pharmaceutical agents for therapies, the study of hepatic pathomechanisms conveyed through microbiological pathogens or hazardous substances, testing of nutrient additives and the development of diagnostics. The system is designed to replace animal experiments in human and veterinary medicine.

BRIEF DESCRIPTION OF THE DRAWINGS

The invention will be described more fully in the following with reference to illustrations and embodiment examples. The drawings show.

DESCRIPTION OF THE EMBODIMENTS

Figure 1:
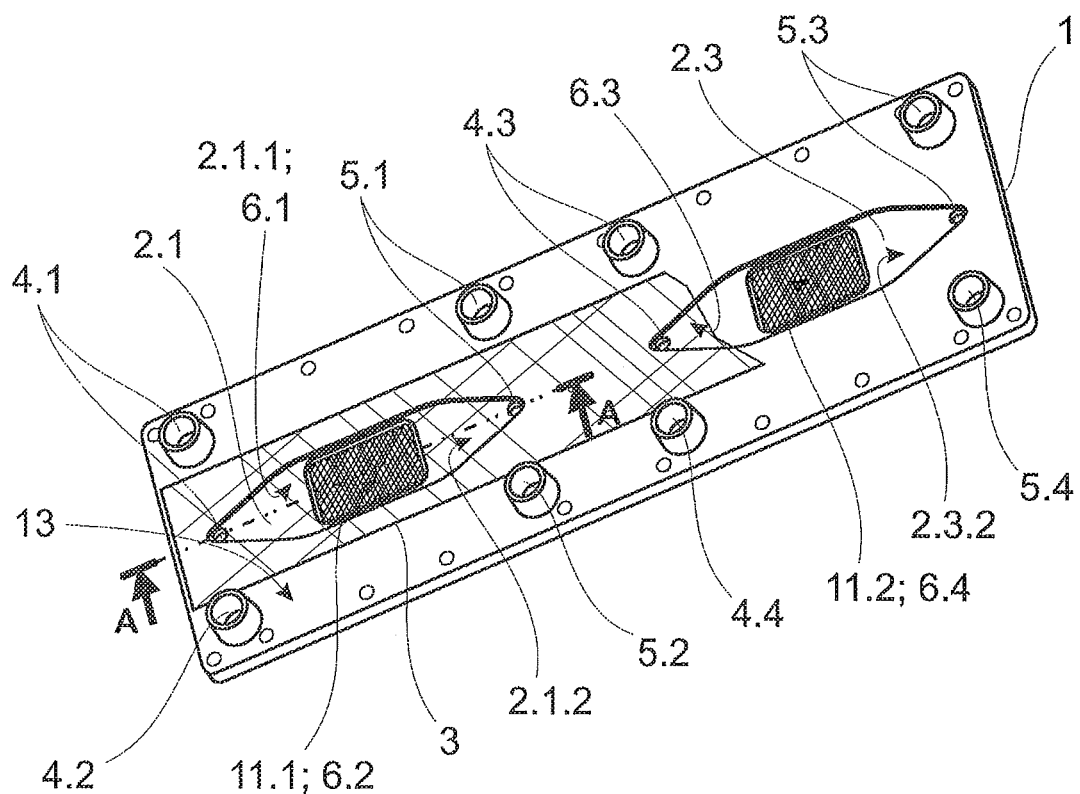
FIG. 1 is a top view of a first embodiment example of a semi-finished product according to the invention with bonding foil partially shown.

In the following embodiment examples, the devices and elements are shown schematically and in a simplified manner. Identical reference numerals designate identical technical features unless otherwise stated. The association of cell layers with determined cell substrates are merely exemplary.

As key elements of a first embodiment example of a semi-finished product according to the invention, FIG. 1 shows a base plate 1, a first well 2.1 and a first inlet opening 4.1 for ingress of a first fluid flow 12.1 (see FIG. 5) into the first well 2.1 and a first outlet opening 5.1 for egress of the first fluid flow 12.1. A first membrane 11.1 is provided between the first well 2.1 and a second well 2.2 (see FIG. 2).

The first well 2.1 narrows to a point at its ends and is approximately rectangular in its middle part. The first inlet opening 4.1 leads into one of the ends terminating in a point, and the first outlet opening 5.1 leads into the other end terminating in a point. This shape results in an extensively laminar flow of the first fluid flow 12.1 through the first well 2.1.

The second well 2.2 is provided on the underside of the base plate 1 (see FIG. 2) which is not visible in FIG. 1. A second inlet opening 4.2 for ingress of a second fluid flow 12.2 (see FIG. 5) into the second well 2.2 and a second outlet opening 5.2 for egress of the second fluid flow 12.2 are provided on the visible upper side.

Figure 4:
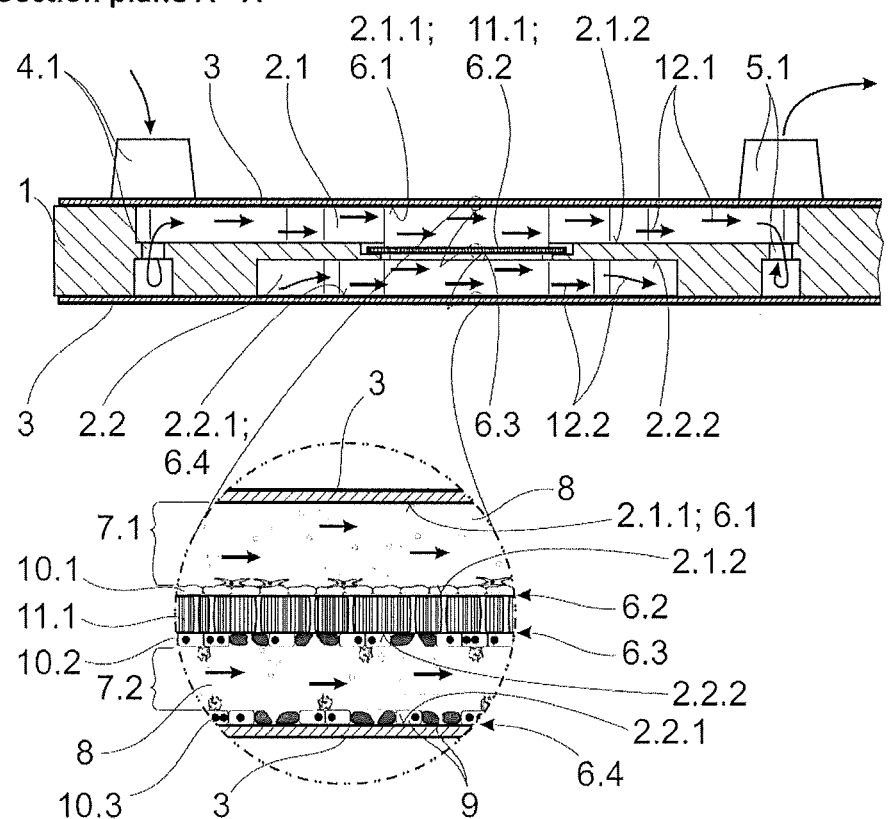
FIG. 4 is an example of cell layers produced according to the invention in a semi-finished product with bonding foil.

A view of a section along section plane A-A is shown in FIG. 4 and described.

In FIG. 1, a third well 2.3 and a fourth well 2.4 (see FIG. 2) are provided on the base plate 1. Also, a third inlet opening 4.3 for ingress of a third fluid flow 12.3 (see FIG. 5) into the third well 2.3, and a third outlet opening 5.3 for egress of the third fluid flow 12.3, and a fourth inlet opening 4.4 for ingress of a fourth fluid flow 12.4 (see FIG. 5) into the fourth well 2.4, and a fourth outlet opening 5.4 for egress of the fourth fluid flow 12.4 are provided. All of the wells 2.1 to 2.4 are surrounded by edges 13 which are formed through the base plate 1.

The semi-finished product is shown in FIG. 1 in a configuration in which the first well 2.1 and the third well 2.3 are sealed in a gas-tight and liquid-tight manner relative to the environment by a bonding foil 3 (shown only partially over well 2.3).

A first wall 2.1.1 constituting a first cell substrate 6.1 is formed through the bonding foil 3 in the first well 2.1. The first membrane 11.1 is held in a second wall 2.1.2. The first membrane 11.1 is part of the second wall 2.1.2 and constitutes a second cell substrate 6.2.

A second membrane 11.2 is arranged between the third well 2.3 and fourth well 2.4 in the same way as that just described.

For simplicity, the first well 2.1 and second well 2.2 (section plane A-A) and associated elements will be referred to in the following. The technical elements of the third well 2.3 and fourth well 2.4 are shown and designated where applicable but are referred to expressly only when required for the explanation.

Figure 2:
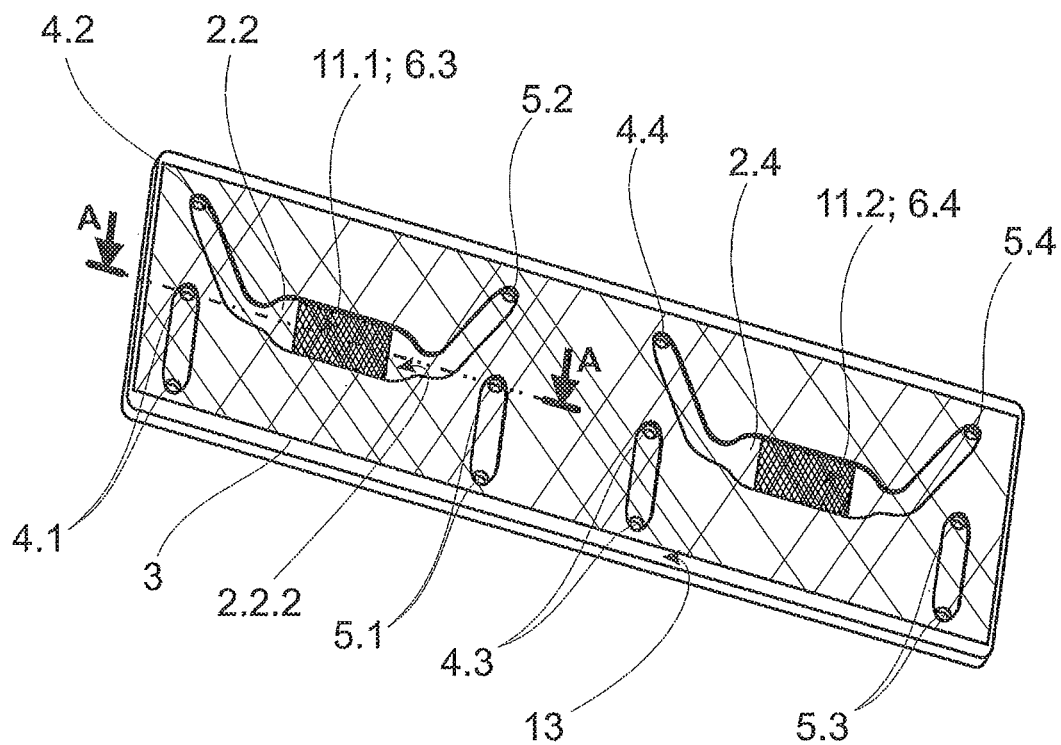
FIG. 2 is a semi-finished product according to the first embodiment example in a view from below with bonding foil.

The underside of the base plate 1 is shown in FIG. 2. The second well 2.2 and the underside of the first membrane 11.1 which serves as third cell substrate 6.3 are visible. This perspective shows a second wall 2.2.2 of the second well 2.2 in which the first membrane 11.1 is held and formed by the back of the second wall 2.1.2 of the first well 2.1 shown in FIG. 1.

The second well 2.2 is approximately rectangular in its middle part, while it is connected to the second inlet opening 4.2 and to the second outlet opening 5.2 through channel-like restrictions.

In further embodiments of the semi-finished product according to the invention, the shapes and dimensions of the wells may be identical to one another.

Figure 3:
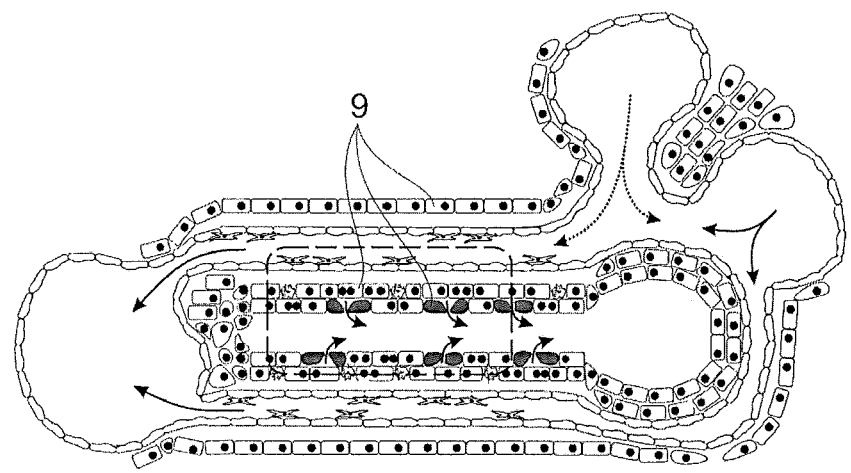
FIG. 3 is an overview of a liver sinusoid.

FIG. 3 schematically shows a liver sinusoid. Cells 9 of different cell types and layered arrangements of the cell types can be seen. Further, flow ratios in the liver sinusoid are shown by arrows. Shown approximately in the middle is an area with a dashed border whose sequence of cell layers is mimicked by a device shown in FIG. 4.

The device according to FIG. 4 is a semi-finished product according to the invention (see FIGS. 1 and 2) which has a bonding foil 3 on its upper side and its lower side, the first well 2.1 and second well 2.2 being sealed against the environment by the bonding foil 3. A first wall 2.1.1 of the first well 2.1, which serves as a first cell substrate 6.1, is formed by the bonding foil 3 on the upper side. A first wall 2.2.1 of the second well 2.2 which serves as a fourth cell substrate 6.4 is formed by the bonding foil 3 on the underside. A first gap 7.1 is provided between the first wall 2.1.1 of the first well 2.1 and the second wall 2.1.2 of the first well 2.1; a second gap 7.2 is provided between the first wall 2.2.1 of the second well 2.2 and the second wall 2.2.2 of the second well 2.2.

In the section shown in enlarged manner, a first to third cell layer 10.1 to 10.3 is shown, these cell layers 10.1 to 10.3 being provided on the second cell substrate 6.2, third cell substrate 6.3 and fourth cell substrate 6.4. An arrangement of cell layers with cells 9 such as is shown in the bordered area in FIG. 3 is replicated by the first to third cell layer 10.1 to 10.3, the first gap 7.1 and the second gap 7.2.

In one possibility for generating the arrangement of cell layers, a cell suspension 8 with cells 9 of the cell type of the first cell layer 10.1 is inserted into the first well 2.1. The second wall 2.1.2 of the first well 2.1, which second wall 2.1.2 is to be colonized, is oriented horizontally and located in a lower position so that the cells 9 are sedimented on the second wall 2.1.2 of the first well 2.1, which second wall 2.1.2 is to be colonized, by the action of gravity. Cells 9 adhere to the upper side of the first membrane 11.1 serving as second cell substrate 6.2 and form the first cell layer 10.1.

Subsequently, a cell suspension 8 with cells of the cell type of the third cell layer 10.3 is inserted into the second well 2.2. Its position remains unchanged. The first wall 2.2.1 of the second well 2.2, which first wall 2.2.1 is to be colonized, is oriented horizontally and located in a lower position so that the cells 9 sediment on the first wall 2.2.1 of the second well 2.2, which first wall 2.2.1 is to be colonized, by the action of gravity. Cells 9 adhere to the first wall 2.2.1 of the second well 2.2 serving as fourth cell substrate 6.4 and form the third cell layer 10.3.

Subsequently, the device is rotated by 180 degrees so that the second well 2.2 is now the upper well. The second wall 2.2.2 of the second well 2.2, which second wall 2.2.2 is to be colonized, is oriented horizontally and is now located in the lower position so that the cells 9 sediment on the second wall 2.2.2 of the second well 2.2, which second wall 2.2.2 is to be colonized, by the action of gravity. Cells 9 adhere to the side of the first membrane 11.1 serving as third cell substrate 6.3 and form the second cell layer 10.2.

To maintain the already existing first cell layer 10.1, the latter is supplied with a suitable fluid, for example, a nutrient medium, in the first well 2.1.

After producing the arrangement of the three cell layers 10.1 to 10.3, the arrangement of the cell layers 10.1 to 10.3 corresponding to the marked area in FIG. 3 is reproduced and an organoid is created.

Figure 5:
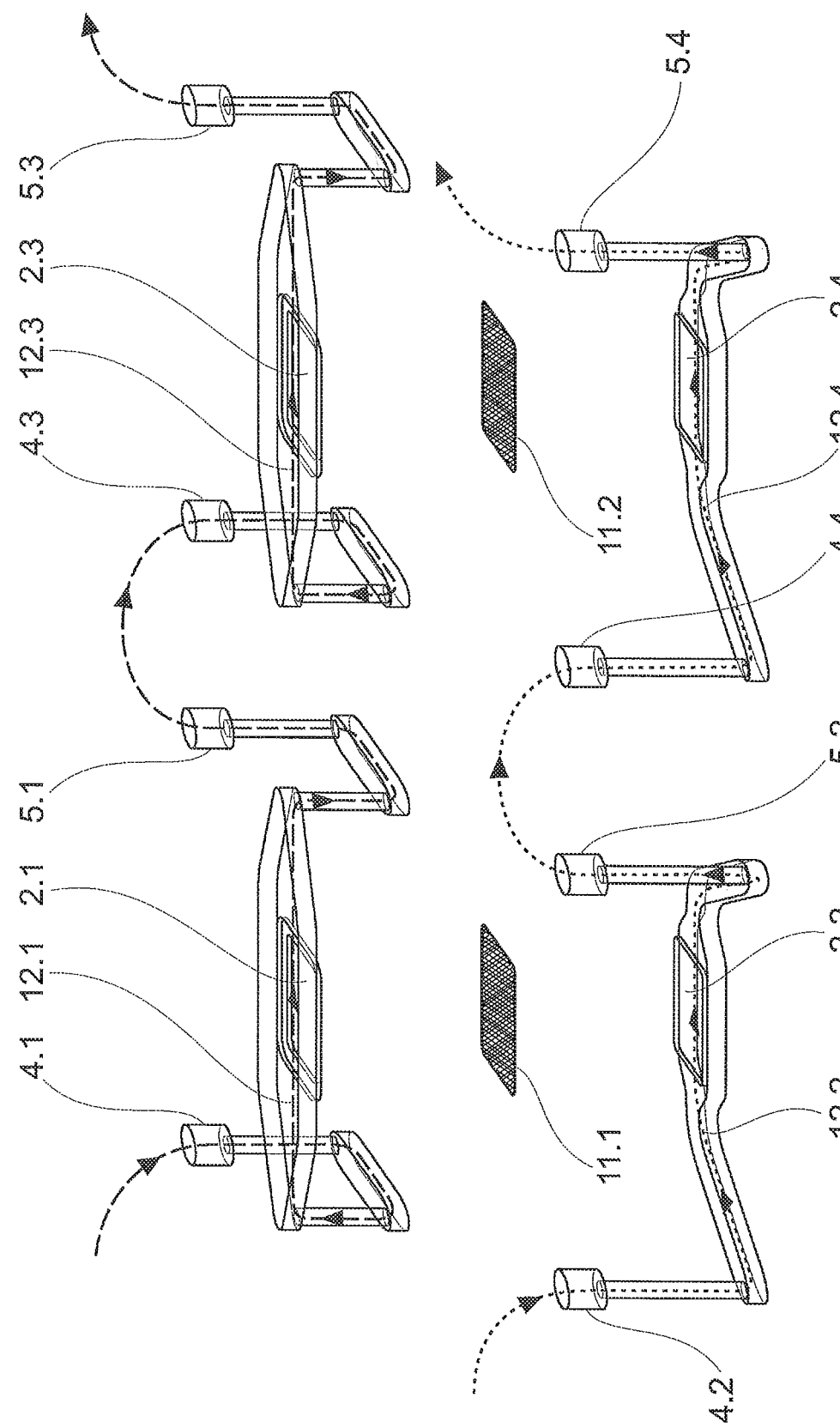
FIG. 5 is a schematic view of the hydraulic linking of four wells.

The four wells 2.1 to 2.4 of a base plate 1 can be hydraulically linked to one another as is shown by way of example schematically in FIG. 5. In this regard, the first outlet opening 5.1 is connected to the third inlet opening 4.3 and the second outlet opening 5.2 is connected to the fourth inlet opening 4.4 so that a first fluid flow 12.1 flows out of the first well 2.1 into the third well 2.3 and flows through the latter as a third fluid flow 12.3. A second fluid flow 12.2 flows through the second well 2.2 and arrives at the fourth inlet opening 4.4 via the second outlet opening 5.2 and into the fourth well 2.4 as fourth fluid flow 12.4.

In further embodiments of the invention, the principle just described can also be used between wells of different base plates 1 or devices (see, for example, FIGS. 6 to 9). Further, the fluid flows 12.1 to 12.4 can be guided differently. Accordingly, the first fluid flow 12.1 can be guided into the fourth well 2.4 and the second fluid flow 12.2 can be guided into the third well 2.3 in a further embodiment of the invention.

It is further possible that the fluid flows 12.1 to 12.4 are guided into one another or are divided and guided into different wells. It is also possible that only portions of the fluid flows 12.1 to 12.4 are guided into subsequent wells. Accordingly, portions of the fluid flows 12.1 to 12.4 can be guided back into the wells that they have just flowed through and can flow through them again.

Figure 6:
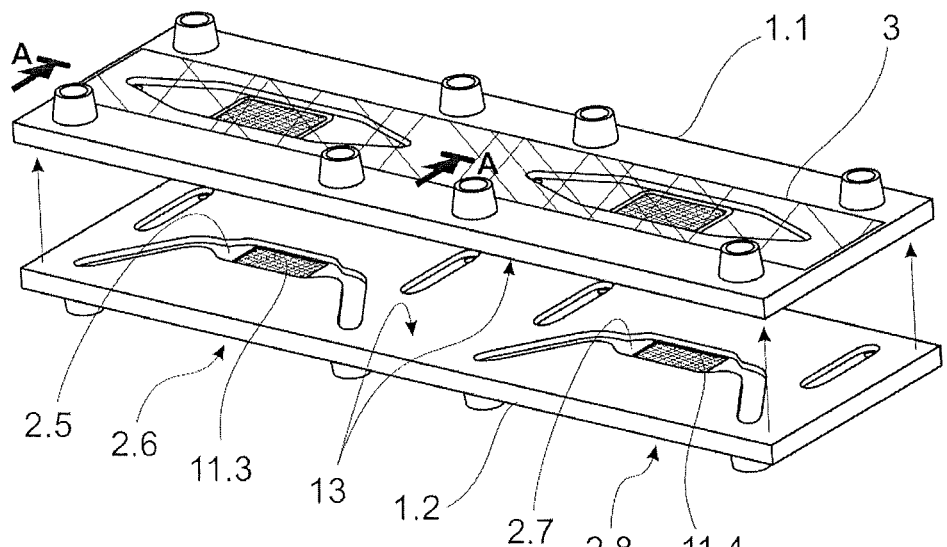
FIG. 6 is a first embodiment example of a device according to the invention.

FIG. 6 shows a first embodiment example of a device according to the invention. A first base plate 1.1 and a second base plate 1.2 are placed against one another with their respective undersides so that the edges 13 of the first base plate 1.1 and second base plate 1.2 touch (the illustration shows a state during assembly). The two base plates 1.1 and 1.2 are sealed at their respective upper sides by bonding foils 3 as has already been described. The second base plate 1.2 likewise has wells which, following the logic described above, are the fifth to eighth wells 2.5 to 2.8 (only the fifth well 2.5 and the seventh well 2.7 are shown; the sixth well 2.6 and the eighth well 2.8 are only referenced by arrows in FIG. 6). The second base plate 1.2 further has a third membrane 11.3 and fourth membrane 11.4. Both base plates 1.1 and 1.2 are connected, e.g., glued, to one another in a liquid-tight manner. The second well 2.2 (see also FIG. 1) and the fourth well 2.4 (see also FIG. 1) of the base plate 1.1 are moved over the fifth well 2.5 or over the seventh well 2.7 of the base plate 11.2 and in each instance form a common well, namely, the fifth well 2.5 and seventh well 2.7, respectively.

Figure 7:
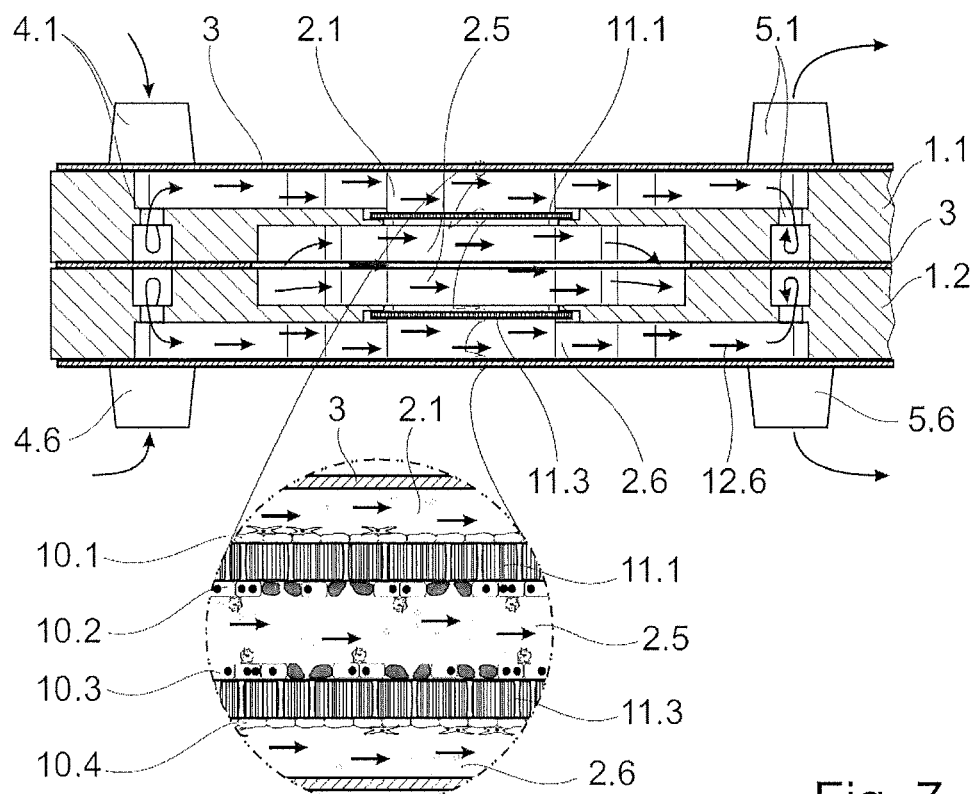
FIG. 7 is a sectional view of the first embodiment example of the device according to the invention with cell layers.

In FIG. 7, the construction of the device according to the invention provided in this way is shown as a sectional diagram along section line A-A (FIG. 6). A first well 2.1 is formed by the first base plate 1.1, shown above. This first well 2.1 is separated from the fifth well 2.5 by the first membrane 11.1. The fifth well 2.5 is in turn separated from the sixth well 2.6 by the third membrane 11.3. A sixth fluid flow 12.6 flows through the sixth well 2.6 via the sixth inlet opening 4.6 and the sixth outlet opening 5.6.

The first well 2.1, fifth well 2.5, sixth well 2.6, first membrane 11.1 and third membrane 11.3 are shown in the section enlargement. A cell layer 10.1 to 10.4 is provided on the two membranes 11.1 and 11.3 on both sides.

Figure 8:
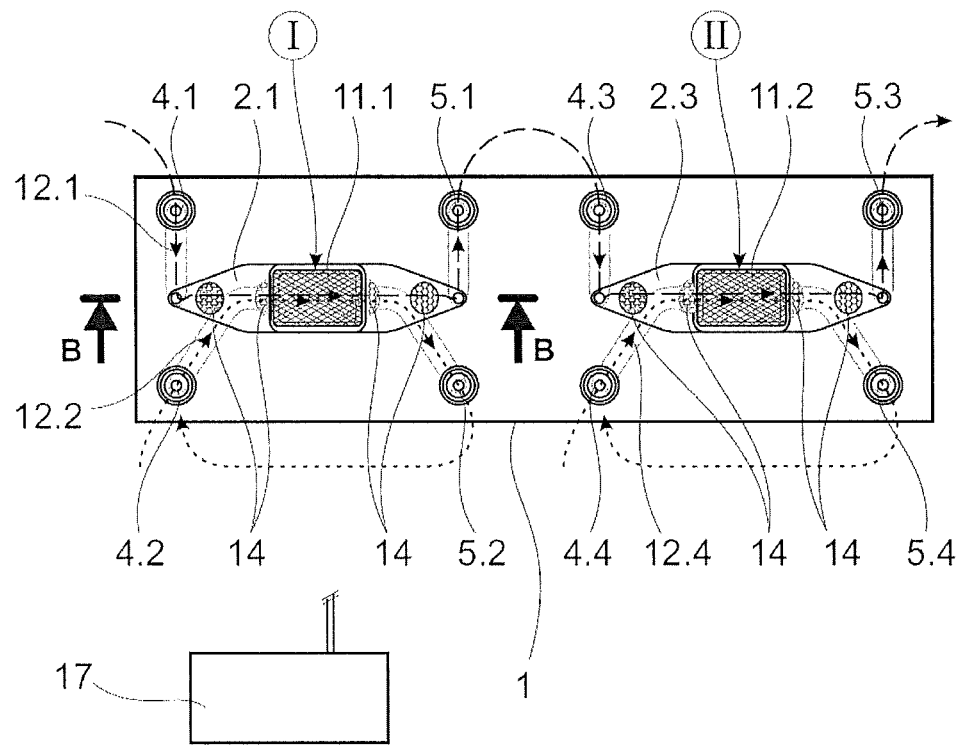
FIG. 8 is a second embodiment example of a device according to the invention with measuring points.

A second embodiment example of a device according to the invention with measuring points 14 is shown in FIG. 8. Measurement points 14 for acquiring measured values based on fluorescing characteristics of constituents of the fluid flows 12.1 to 12.4 (see, e.g., FIG. 5) are arranged on the base plate 1 configured according to FIG. 1 in every well 2.1 to 2.4 (only the first well 2.1 and the third well 2.3 are shown). They are data-communicatively connected to an evaluating and controlling unit 17 by means of which the composition, the pressure and the temperature of the fluid flows 12.1 to 12.4 can be adjusted so as to be controlled on the basis of the acquired measurement data. Further, measurement data for further evaluations are stored for later recall. The measurement points 14 serve for contactless measurement of glucose and partial oxygen consumption of the cells 9 of the cell layers.

An organoid of the liver (liver organoid I) is provided according to the described method in the first well 2.1 and second well 2.2, while an organoid of the intestine (intestinal organoid II) is provided in the third well 2.3 and fourth well 2.4. The first outlet opening 5.1 is hydraulically connected to the third inlet opening 4.3. Through the second inlet opening 4.2, a second fluid flow 12.2 is fed to the second well 2.2 for supplying the cell layers in the second well 2.2 and the cell layers on the first membrane 11.1 in the first well 2.1. The second fluid flow 12.2 is guided out via the second outlet opening 5.2 and is mixed in portions with fresh fluid before this mixture arrives in the second well 2.2 again via the second inlet opening 4.2. The same applies for the fourth well 2.4. Through the first inlet opening 4.1, a first fluid flow 12.1 is guided through the first well 2.1 to the first outlet opening 5.1 and, from there, travels via the third inlet opening 4.3 into the third well 2.3, flows through the latter as third fluid flow 12.3 and is guided out via the third outlet opening 5.3. Through this configuration, organoids and their physiological effects on one another are simulated in vitro in an experimental environment and can be acquired and evaluated.

Figure 9:
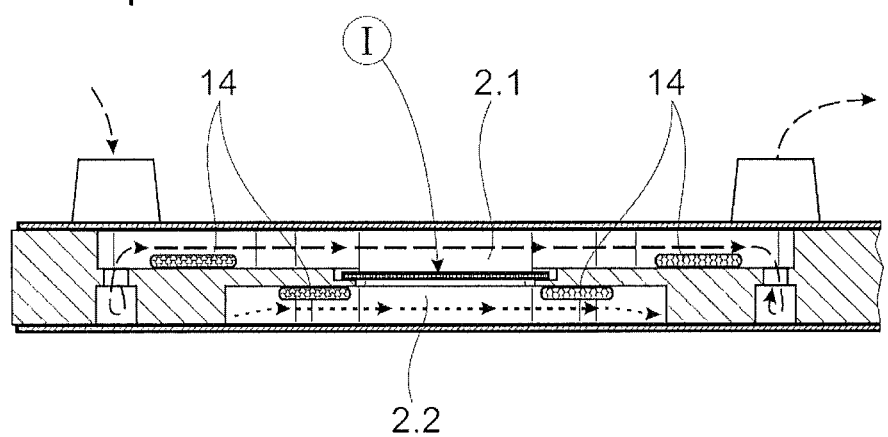
FIG. 9 is a sectional view of the second embodiment example of the device according to the invention with cell layers.

In FIG. 9, the placement of the measurement points 14 in the first well 2.1 and in the second well 2.2 is shown in a sectional view along section plane B-B (see FIG. 8). Areas of the liver organoid or intestinal organoid are designated by Roman numerals I and II and are shown enlarged in FIG. 10.

Figure 10:
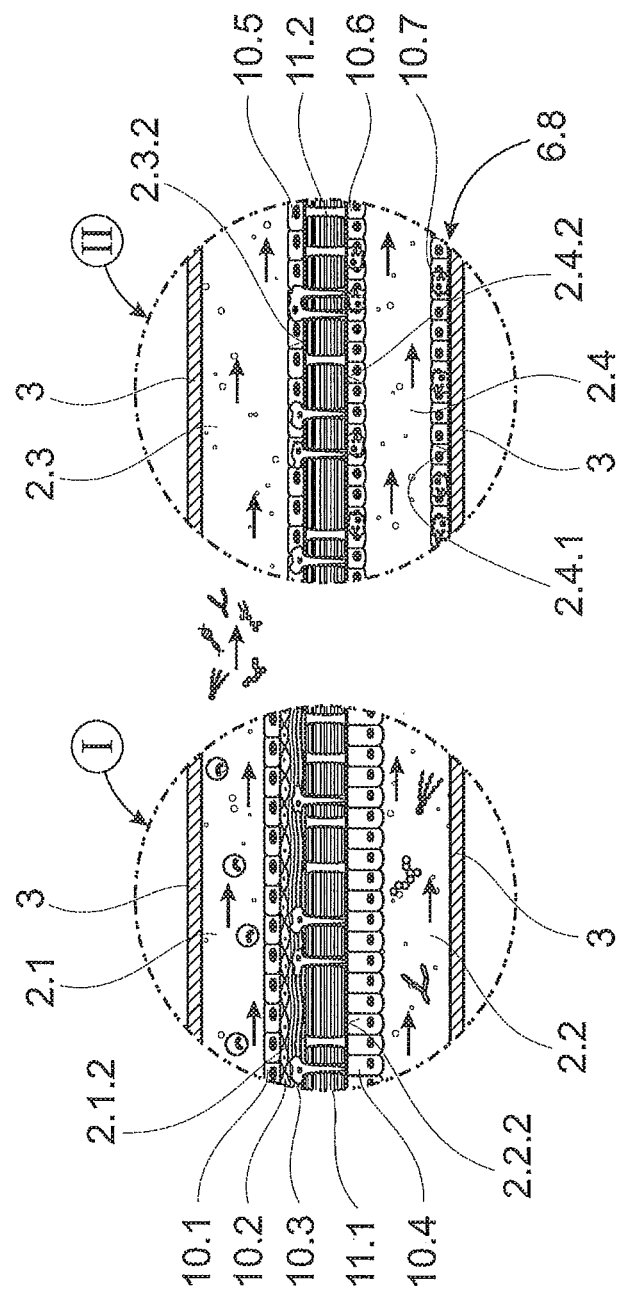
FIG. 10 is a schematic view of the cell layers in the wells of the second embodiment example of the device according to the invention.

The liver organoid I is shown in the section enlargement on the left-hand side in FIG. 10. On the second wall 2.1.2 of the first well 2.1 on the first membrane 11.1, there is a first cell layer 10.1 as a HIMEC (Human Intestinal Microvascular Endothelial Cells) layer over a second cell layer 10.2 FB (fibroblasts) and a third cell layer 10.3 ECM (extracellular matrix). On the second wall 2.2.2 of the second well 2.2 on the first membrane 11.1, there is a fourth cell layer 10.4 HCEC (Human Colon Epithelial Cells, human intestinal epithelial cells).

The intestinal organoid II is shown in the section enlargement on the right-hand side in FIG. 10. On the second wall 2.3.2 of the third well 2.3 on the second membrane 11.2, there is a fifth cell layer 10.5 as a HSEC (Human Sinusoidal Endothelial Cell) layer. This is interspersed with moMΦ cells (primary human monocyte derived macrophages) which were colonized as co-culture. On the second wall 2.4.2 of the fourth well 2.4 on the second membrane 11.2, there is a sixth cell layer 10.6 HSC (human stellate cells). On the first wall 2.4.1 of the fourth well 2.4, which first wall 2.4.1 serves as eighth cell substrate 6.8, there is a HHC (human differentiated hepatocytes) layer as seventh cell layer 10.7, and this is interspersed with co-cultured BC (bile canaliculi).

In further embodiments, there may be more cell layers 10.1, 10.2, . . . which, in addition, can have cells 9 of other cell types, other sequences of cell layers and/or other arrangements of cell layers 10.1, 10.2, . . . on the various cell substrates 6.1, 6.2. . . .

Figure 11:
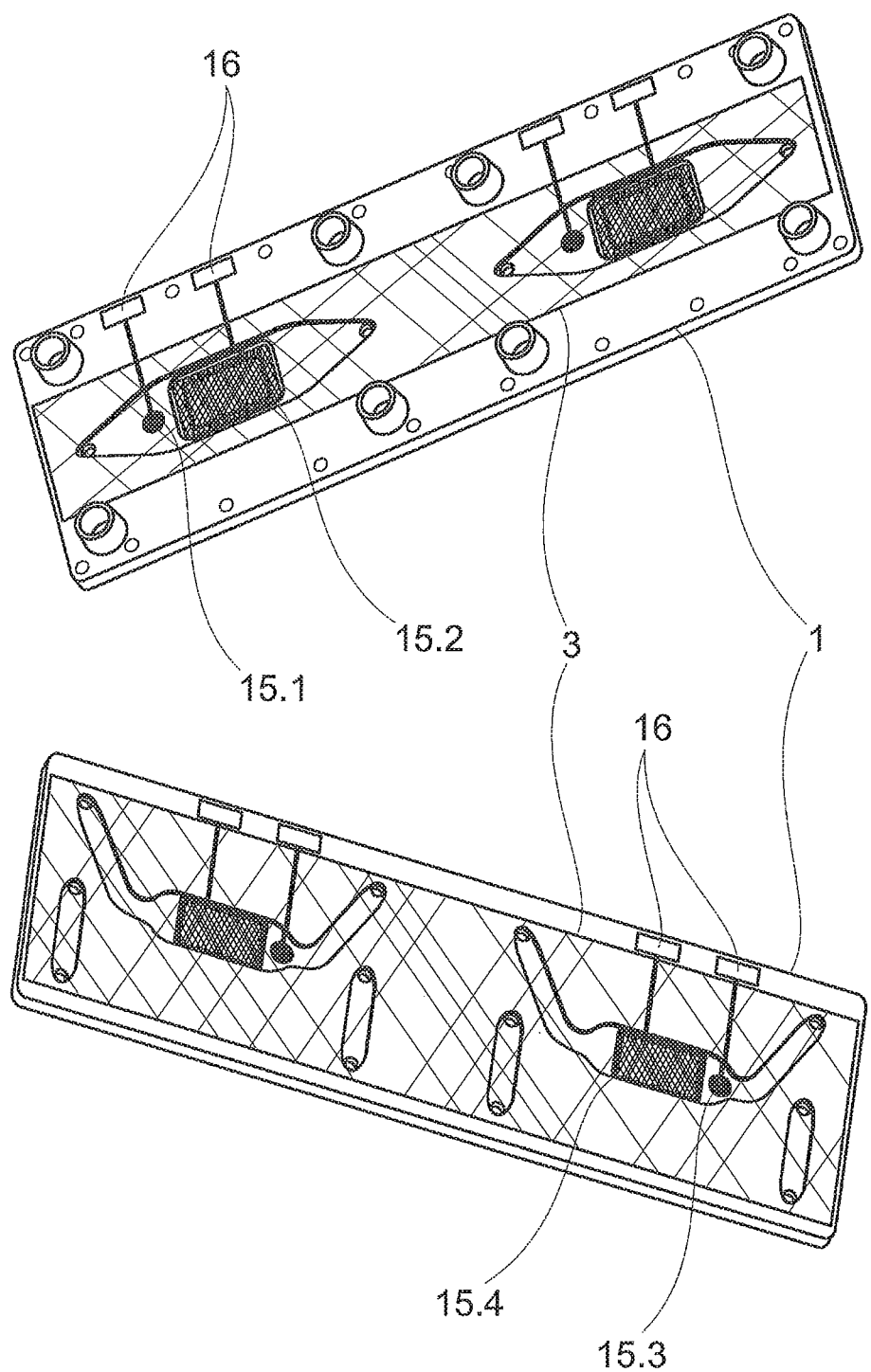
FIG. 11 is a schematic view of a first electrode arrangement.

One possibility for acquiring measurement data at semi-finished products according to the invention and at devices according to the invention is shown schematically in FIG. 11. A first current-supplying electrode 15.1 and a first measurement electrode 15.2 are arranged at the upper side of the base plate 1. A second current-supplying electrode 15.3 and a second measurement electrode 15.4 are arranged at the underside of the base plate 1. These electrodes 15.1, 15.2 and 15.3, 15.4 are printed on a bonding foil 3. In further embodiments, they can also be integrated in or arranged, for example, printed, on the base plate 1. Each electrode 15.1 to 15.4 has a contacting surface 16 for electrical and/or measuring contact.

By applying voltage to the electrodes 15.1 to 15.4, measurement data of acquired electric voltages, electric currents, ohmic resistances and/or impedances can be obtained and evaluated.

The electrodes 15.1 to 15.4, e.g., for impedance measurement, are arranged, for example, sintered or pressed, on the bonding foils 3 directly above and below the first membrane 11.1 and/or second membrane 11.2. The supply of alternating current for building up an electrical field is carried out on the contacting surfaces 16. The two current-supplying electrodes 15.1 and 15.3 lie opposite one another, for example, in the first well 2.1 on the liquid-supplying side and in the second well 2.2 on the liquid-removal side.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

LIST OF REFERENCE CHARACTERS

1 base plate
1.1 first base plate
1.2 second base plate
2.1 first well
2.1.1 first wall (of the first well 2.1)
2.1.2 second wall (of the first well 2.1)
2.2 second well
2.2.1 first wall (of the second well 2.2)
2.2.2 second wall (of the second well 2.2)
2.3 third well
2.3.2 second wall (of the third well 2.3)
2.4 fourth well
2.4.1 first wall (of the fourth well 2.4)
2.4.2 second wall (of the fourth well 2.4)
2.5 fifth well
2.6 sixth well 2.7 seventh well
2.8 eighth well
3 bonding foil
4.1 first inlet opening
4.2 second inlet opening
4.3 third inlet opening
4.4 fourth inlet opening
4.6 sixth inlet opening
5.1 first outlet opening
5.2 second outlet opening
5.3 third outlet opening
5.4 fourth outlet opening
5.6 sixth outlet opening
6.1 first cell substrate
6.2 second cell substrate
6.3 third cell substrate
6.4 fourth cell substrate
6.8 eighth cell substrate
7.1 first gap
7.2 second gap
8 cell suspension
9 cells
10.1 first cell layer
10.2 second cell layer
10.3 third cell layer
10.4 fourth cell layer
10.5 fifth cell layer
10.6 sixth cell layer
10.7 seventh cell layer
11.1 first membrane
11.2 second membrane
11.3 third membrane
11.4 fourth membrane
12.1 first fluid flow
12.2 second fluid flow
12.3 third fluid flow
12.4 fourth fluid flow
12.6 sixth fluid flow
13 edges
14 measurement points
15.1 first current-supplying electrode
15.2 first measurement electrode
15.3 second current-supplying electrode
15.4 second measurement electrode
16 contacting surface
17 evaluating and controlling unit
I liver organoid
II intestinal organoid

What is claimed is:

1. Semi-finished products for a device, having one or at least two of said semi-finished products mounted one above the other, for in vitro production and culturing of cell layers, said semi-finished products having a first and a second well which are arranged one above the other in a single base plate which has an upper side and a lower side, said first well being formed in the upper side of the single base plate and the second well being formed in the lower side of the single base plate, said first and second wells being separated from one another by a single porous membrane with two lateral surfaces and sealed against the environment by a bonding foil on the upper side and a bonding foil on the lower side, wherein a first wall of the first well is formed as a first cell substrate by the bonding foil on the upper side and a first wall of the second well is formed as a fourth cell substrate by the bonding foil on the lower side and a second wall of the first well is formed as a second cell substrate through one of the lateral surfaces of the membrane and a second wall of the second well is formed as a third cell substrate through the other of the lateral surfaces of the membrane; the first well is formed so as to narrow to a point at its ends and to be rectangular in its middle part, and one of the ends terminating in a point leads into a first inlet opening for ingress of a first fluid flow into the first well and the other of the ends terminating in a point leads into a first outlet opening for egress of the first fluid flow out of the first well; the second well is rectangular and is connected to a second inlet opening for ingress of a second fluid flow into the second well and a second outlet opening for egress of the second fluid flow out of the second well through channel-like restrictions.

* * * * *